(12) United States Patent
Betz et al.

(10) Patent No.: US 8,298,264 B2
(45) Date of Patent: Oct. 30, 2012

(54) SYSTEMS AND METHODS FOR USE IN SPINAL SUPPORT

(75) Inventors: Randal Betz, Ocean City, NJ (US); Fred J Molz, Birmingham, AL (US); Jeff R. Justis, Germantown, TN (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 894 days.

(21) Appl. No.: 11/470,837

(22) Filed: Sep. 7, 2006

(65) Prior Publication Data

US 2008/0065069 A1    Mar. 13, 2008

(51) Int. Cl.
*A61B 17/70* (2006.01)

(52) U.S. Cl. .......... 606/246; 606/79; 606/256; 606/259; 606/279

(58) Field of Classification Search .......... 606/53, 606/60, 246, 259, 261, 262, 86, 254, 255, 606/258, 250–253, 256, 257, 260, 263–279; 623/17.12

See application file for complete search history.

(56) References Cited

U.S. PATENT DOCUMENTS

| | | | | |
|---|---|---|---|---|
| 3,846,846 A * | 11/1974 | Fischer | ...... | 623/23.18 |
| 3,858,578 A * | 1/1975 | Milo | ...... | 600/229 |
| 4,078,559 A | 3/1978 | Nillinen | ...... | 128/69 |
| 4,422,451 A | 12/1983 | Kalamchi | ...... | 128/69 |
| 4,643,178 A | 2/1987 | Nastari et al. | ...... | 128/92 |
| 4,719,905 A | 1/1988 | Steffee | ...... | 128/69 |
| 5,007,909 A * | 4/1991 | Rogozinski | ...... | 606/277 |
| 5,645,545 A * | 7/1997 | Bryant | ...... | 606/62 |
| 5,649,925 A | 7/1997 | Barbera Alacreu | ...... | 606/61 |
| 5,658,286 A | 8/1997 | Sava | ...... | 606/61 |
| 5,944,719 A * | 8/1999 | Leban | ...... | 606/59 |
| 6,056,749 A * | 5/2000 | Kuslich | ...... | 606/86 A |
| 6,296,644 B1 | 10/2001 | Saurat et al. | ...... | 606/61 |
| 6,387,130 B1 * | 5/2002 | Stone et al. | ...... | 623/17.16 |
| 6,475,220 B1 | 11/2002 | Whiteside | ...... | 606/74 |
| 6,623,484 B2 | 9/2003 | Betz et al. | ...... | 606/61 |
| 6,740,090 B1 * | 5/2004 | Cragg et al. | ...... | 606/79 |
| 6,790,210 B1 | 9/2004 | Cragg et al. | ...... | 606/80 |
| 6,899,716 B2 * | 5/2005 | Cragg | ...... | 606/86 R |
| 6,923,811 B1 * | 8/2005 | Carl et al. | ...... | 623/17.11 |
| 6,989,011 B2 | 1/2006 | Paul et al. | ...... | 606/61 |
| 7,585,300 B2 * | 9/2009 | Cha | ...... | 606/80 |
| 7,785,325 B1 * | 8/2010 | Milbank | ...... | 606/62 |
| 2003/0195518 A1 * | 10/2003 | Cragg | ...... | 606/80 |
| 2003/0204189 A1 * | 10/2003 | Cragg | ...... | 606/61 |
| 2003/0220643 A1 | 11/2003 | Ferree | ...... | 606/61 |
| 2003/0220646 A1 * | 11/2003 | Thelen et al. | ...... | 606/79 |
| 2003/0229353 A1 * | 12/2003 | Cragg | ...... | 606/86 |
| 2004/0106921 A1 | 6/2004 | Cheung et al. | ...... | 606/61 |
| 2004/0133204 A1 * | 7/2004 | Davies | ...... | 606/63 |
| 2004/0220577 A1 * | 11/2004 | Cragg et al. | ...... | 606/80 |
| 2004/0249464 A1 * | 12/2004 | Bindseil et al. | ...... | 623/17.16 |
| 2005/0136764 A1 | 6/2005 | Sherman et al. | ...... | 442/103 |

(Continued)

FOREIGN PATENT DOCUMENTS

WO    WO 2004/082464 A2    9/2004

*Primary Examiner* — Alvin Stewart
*Assistant Examiner* — Jerry Cumberledge

(57) ABSTRACT

A method for supporting a spine of a person includes forming a pathway in a spine by removing a plurality of portions of a plurality of vertebrae of the spine with the pathway being configured to receive a supporting structure. The supporting structure is inserted into the pathway and through the plurality of vertebrae.

25 Claims, 5 Drawing Sheets

U.S. PATENT DOCUMENTS

| | | | |
|---|---|---|---|
| 2005/0165406 A1* | 7/2005 | Assell et al. | 606/86 |
| 2005/0177157 A1* | 8/2005 | Jahng | 606/61 |
| 2005/0261695 A1* | 11/2005 | Cragg et al. | 606/86 |
| 2006/0009767 A1 | 1/2006 | Kiester | 606/61 |
| 2006/0016054 A1 | 1/2006 | Muzzillo | 27/21.1 |
| 2006/0265077 A1* | 11/2006 | Zwirkoski | 623/17.16 |
| 2009/0171151 A1* | 7/2009 | Choset et al. | 600/114 |

\* cited by examiner

SYSTEMS AND METHODS FOR USE IN SPINAL SUPPORT

TECHNICAL FIELD

The present invention relates generally to the field of surgery and medical implants, and more particularly, to surgical tools and methods for supporting a spine.

BACKGROUND OF THE INVENTION

The human spine is a biomechanical structure with thirty-three vertebral members, and is responsible for protecting the spinal cord, nerve roots and internal organs of the thorax and abdomen. The spine also provides structure support for the body while permitting flexibility of motion. A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition.

Back problems sometimes require correcting the curvature of the spine and/or supporting some or all of the spine to minimize pain to the patient. Such conditions include scoliosis, acute fractured collapsing disc, kyphosis and spinal osteo-arthritis, among others.

Thus, a need continues to exist for enhanced systems and methods for supporting and/or correcting a curvature of the spine. The systems and methods disclosed herein address these needs.

SUMMARY OF THE INVENTION

The shortcomings of the prior art are overcome and additional advantages are provided, in one aspect, through a method for use in supporting a spine which includes forming a pathway in the spine by removing a plurality of portions of a plurality of vertebrae of the spine, and the pathway being configured to receive a supporting structure. The supporting structure is inserted into the pathway and through the plurality of vertebrae.

In another aspect the present invention provides a spine-supporting structure system which includes a supporting structure for supporting a spine and a pathway through a plurality of vertebrae of the spine. The supporting structure is inserted into the pathway and through the plurality of vertebrae to support the spine.

In yet another aspect the present invention provides a supporting structure for a spine which includes a plurality of segments configured to form a supporting structure configured to be inserted into a spinal pathway created in a plurality of vertebrae of the spine. A first segment of the plurality of segments has a first end and a second end. A second segment of the plurality of segments has a third end and a fourth end. The first end is engageable with the third end to connect the first segment to the second segment. A cord is received in a first interior of the first segment and a second interior of the second segment. The cord is coupled to the first segment and the second segment and provides stiffness to the first segment and the second segment to support the spine of the person when the plurality of segments is inserted into the spinal pathway.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be apparent from the following detailed description of preferred embodiments taken in conjunction with the accompanying drawings in which:

BEST MODE FOR CARRYING OUT THE INVENTION

In accordance with the principles of the present invention, a spinal supporting system, and methods for use in supporting a spine, are provided.

Figure 1:
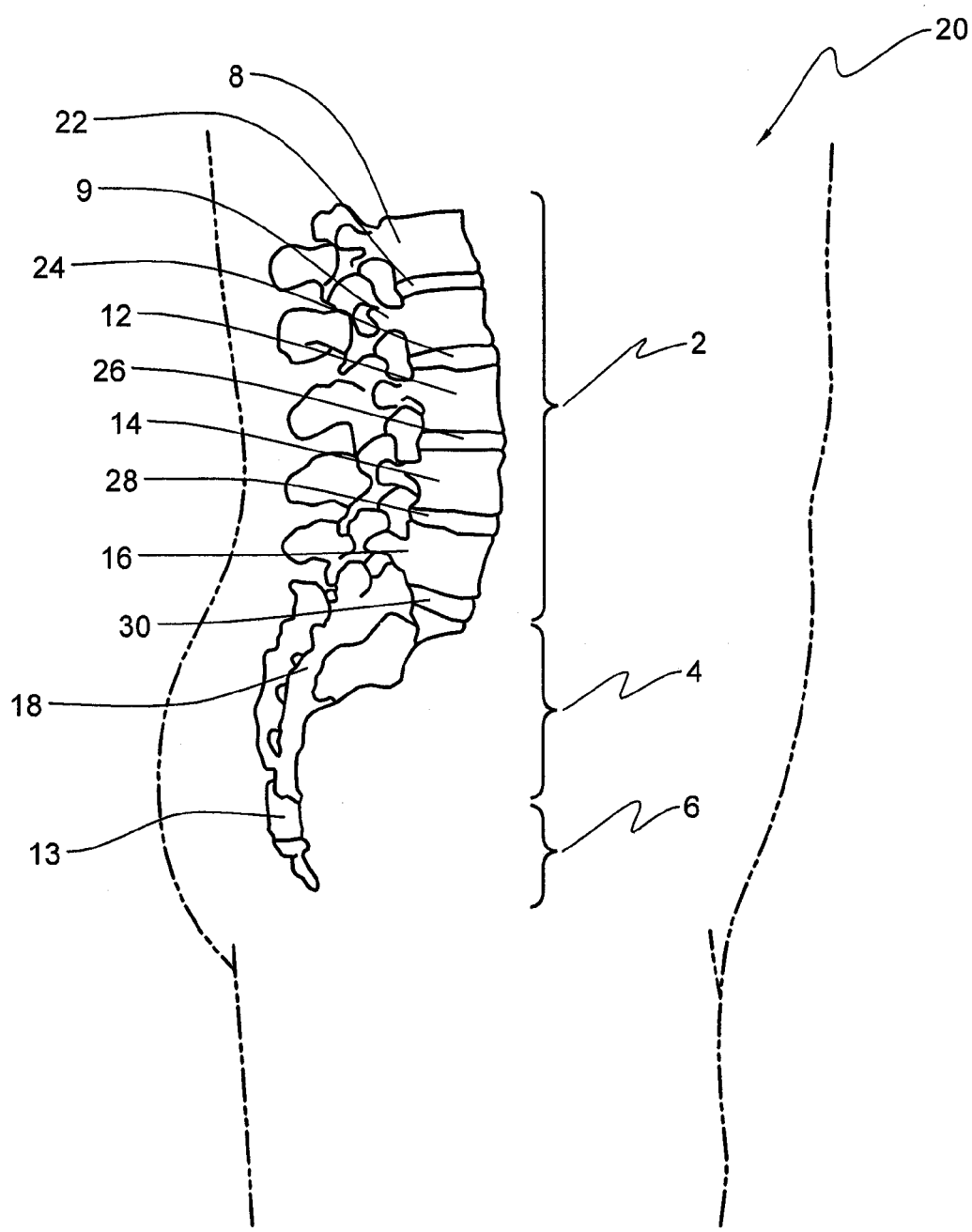
FIG. 1 is a side elevational view of a lower portion of the spine of a human.

Referring to FIG. 1, a portion of a spinal column 20 is shown. As depicted, spinal column 20 includes a lumbar region 2, a sacral region 4, and a coccygeal region 6. As is known in the art, spinal column 20 also includes a cervical region and a thoracic region. For clarity and ease of discussion, the cervical region and the thoracic region are not illustrated.

As depicted in FIG. 1, lumbar region 2 includes a first lumbar vertebra 8, a second lumbar vertebra 9, a third lumbar vertebra 12, a fourth lumbar vertebra 14, and a fifth lumbar vertebra 16. Sacral region 4 includes a sacrum 18. Further, coccygeal region 6 includes a coccyx 13. As depicted in FIG. 1, a first intervertebral lumbar disc 22 is disposed between the first lumbar vertebra 8 and the second lumbar vertebra 9. A second intervertebral lumbar disc 24 is disposed between the second lumbar vertebra 9 and the third lumbar vertebra 12. A third intervertebral lumbar disc 26 is disposed between third lumbar vertebra 12 and fourth lumbar vertebra 14. Further, a fourth intervertebral lumbar disc 28 is disposed between fourth lumbar vertebra 14 and the fifth lumbar vertebra 16.

Additionally, a fifth intervertebral lumbar disc 30 is disposed between fifth lumbar vertebra 16 and the sacrum 18.

Figure 2:
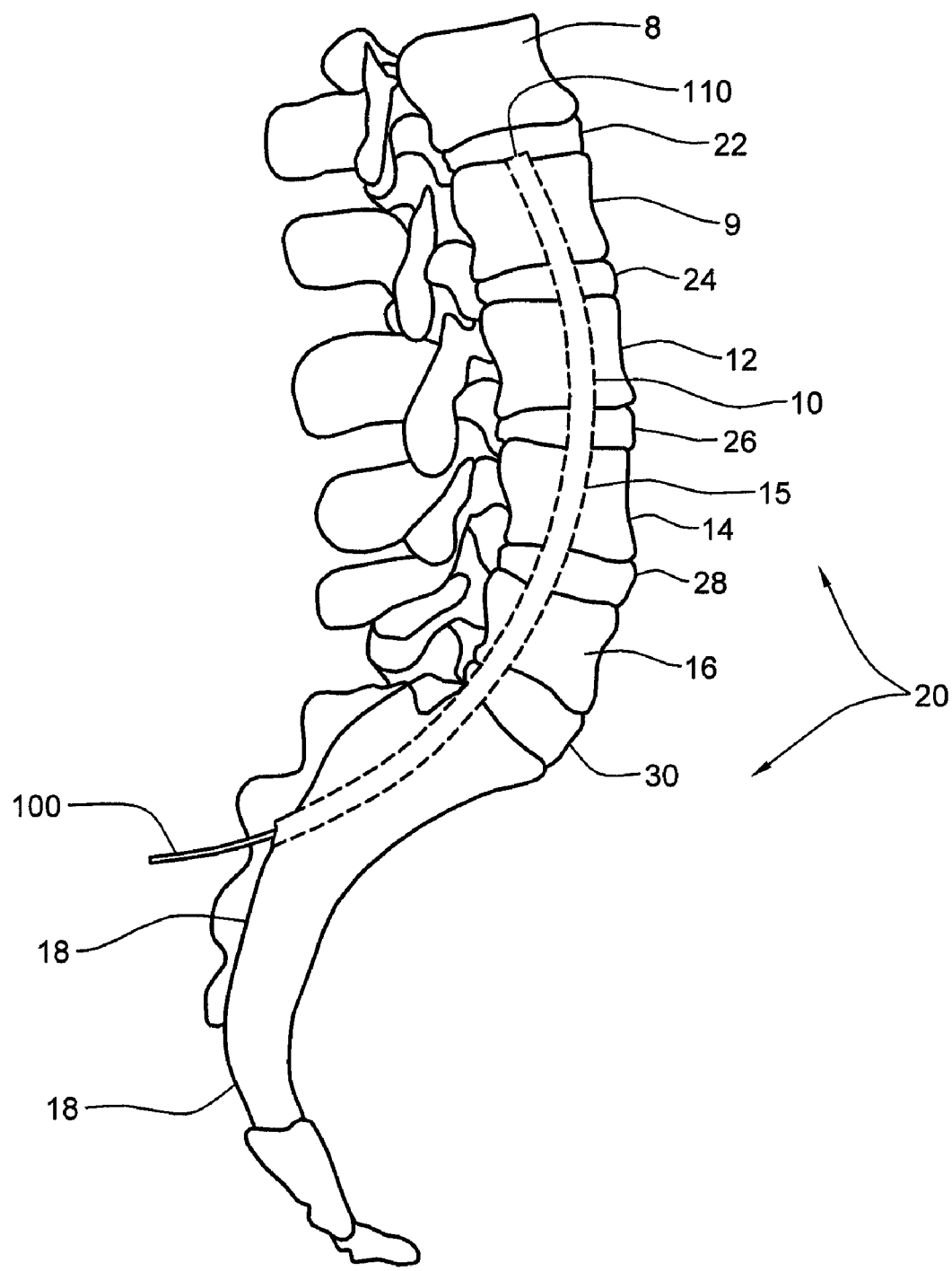
FIG. 2 is a cross-sectional view of the portion of the spine of FIG. 1 further including a supporting structure inserted into the spine, in accordance with an aspect of the present invention.

As depicted in FIG. 2, a system or structure 10 for supporting spinal column 20, or a portion thereof, may be inserted into a pathway 15 or channel in spinal column 20. Pathway 15 may be cylindrical and may extend through one or more portions of spinal column 20. For example, pathway 15 may extend percutaneously through intervertebral disc(s) and vertebral bod(ies) of spinal column 20. For example, pathway 15 may extend through sacrum 18, fifth lumbar vertebra 16, fourth lumbar vertebra 14, third lumbar vertebra 12, and to a top extent of second lumbar vertebra 9 as depicted in FIG. 2.

Figure 3:
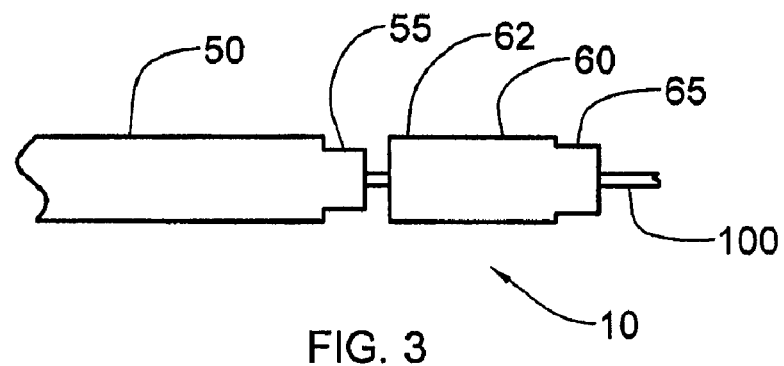
FIG. 3 is a side elevational view of a portion of the supporting structure of FIG. 2, in accordance with an aspect of the present invention.
Figure 4:
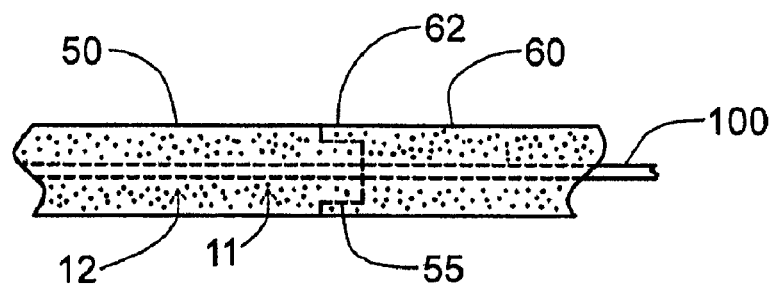
FIG. 4 is another side elevational view of a portion of the supporting structure of FIG. 3 further showing interior details in phantom, in accordance with an aspect of the present invention.

A spinal supporting structure (e.g., supporting structure 10) may be made up of a plurality of segments engaged with one another to provide support to the spine and/or promote a desired spinal curvature. For example, structure 10 may include a first segment 50 and second segment 60 as depicted in FIGS. 3-4. The segments may be engageable with one another such that the segments provide structural support to one another and a spinal column (e.g., spinal column 20, FIGS. 1-2) when they are inserted therein. For example, segment 50 may include a narrowed end 55 receivable within a receiving end 62 of segment 60 wherein receiving end 62 has a diameter slightly larger than narrowed end 55. Second segment 60 may also have a narrowed end 65 receivable within a receiving end (not shown) of another segment (not shown) of a spinal supporting structure (e.g., supporting structure 10). Further segments may be connected to one another in a similar manner to form a supporting structure (e.g., supporting structure 10). Alternatively, such segments could be connected in a different manner. For example, in an unillustrated embodiment one end of each individual segment could include an outer thread while an opposite end could include an internal thread such that the segment could be connected on each end to other such threaded segments.

Supporting structure 10 may also include a cord 100 configured to allow the stiffening or tightening of a plurality of segments (e.g., segment 50 and segment 60) connected to one another. For example, cord 100 may be connected to one or more ends (e.g. a first end 110) of supporting structure 10. The plurality of segments may be loosely or flexibly connected to one another as depicted for example relative to segment 50 and segment 60 in FIG. 3. By applying tension to cord 100 and/or applying opposing pressure to one or more segments (e.g., segment 50 and segment 60) of a supporting structure (e.g., support structure 10), the supporting structure may be stiffened and may provide support to one or more vertebrae or portions along spine 20. For example, such a stiffening or tightening of supporting structure 10 may cause first segment 50 and second segment 60 to engage and abut one another such that narrowed end 55 is received in receiving end 62. Such stiffening or tightening may also cause supporting structure 10 as a whole to form a desired shape for promoting a correct curvature of the spine. Cord 100 may also hold together the segments making up supporting structure 10 while allowing flexibility to allow freedom of movement of a patient having the supporting structure inserted into his/her spinal column. For example, cord 100 could be flexible and/or resilient to allow the segments making up the support structure to be held together while still allowing movement between the segments thereby allowing freedom of movement for the patient. In another example, the cord could be more rigid to minimize such flexibility and freedom of movement between the segments.

A supporting structure (e.g., supporting structure 10) could be inserted into the spinal column to provide support and/or a correct curvature thereto as described. More specifically, the placement of the supporting structure within the pathway (e.g., pathway 15) allows the supporting structure to directly support the vertebrae of spinal column 20 by direct contact therewith. For example, the frictional contact of the supporting structure with the spinal column may provide support thereto to correct the curvature and/or vertically support portions of spinal column 20. Further, an end (e.g., end 110) of the supporting structure (supporting structure 10) may directly vertically support a portion (e.g., second lumbar vertebra 9 as depicted in FIG. 2) of the spinal column which it contacts. Also, the supporting structure could remain permanently within the spinal column to provide the support and/or promote the correct curvature of the spine. Alternatively, the supporting structure could be removed when the correct curvature of the spine has been achieved or support for the spine is no longer needed. Further, a supporting structure may be removed and another substituted therefor in the event that a different curvature promoting feature or different supporting structure is desired. For example, the curvature of a portion of a spine may be corrected while another requires further correction. In such a situation, a supporting structure may be substituted by another supporting structure of a different shape and/or size.

Figure 5:
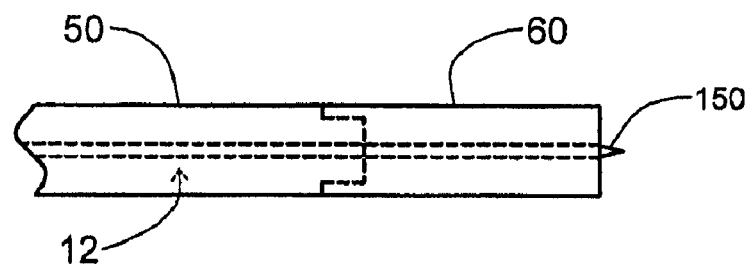
FIG. 5 is a side elevational view of another embodiment of a portion of a supporting structure further including a cutting tool, in accordance with an aspect of the present invention.

An end of a supporting structure (e.g., supporting structure 10) may also include a cutting tool for removing portions of the spine to create a pathway for the supporting structure therein. For example, second segment 60 could include a cutting end 150 as depicted in FIG. 5. A supporting structure (e.g., support structure 10) may be rotated by a user (e.g., a surgeon) to cause the rotation of cutting end 150 to create the pathway (e.g., pathway 15) through the bodies of the spinal column. The supporting structure may be removed from the pathway to allow cutting end 150 to be removed therefrom and the supporting structure (e.g., supporting structure 10) could then be reinserted into the pathway (e.g., pathway 15) to provide desired support and/or curvature correction. Alternatively, a cutting end (e.g., cutting end 150) may be connected to the supporting structure such that the cutting end may be removed via a cord through the interior of the supporting structure. As described above, in one unillustrated embodiment the segments may be connected to one another via threaded connections, and such threadedly connected segments may be rotated to allow the movement of such a cutting tool (e.g., cutting end 150) to create a pathway, such as pathway 15. Further, in another unillustrated example a cutting end or mechanism (not shown) could be remotely powered via a power cord (not shown) running through the interior of the supporting structure.

Also, after supporting structure 10 has been inserted into pathway 15, a flowable curable biocompatible material 11 may be injected or inserted into an interior 12 (FIGS. 4-5) of supporting structure 10. The curable material may provide further structure and/or resiliency to the supporting structure. For example, the curable material could be a rapidly curing, tear resistant elastomer, such as a silicone material. Such a curable material may be used in conjunction with, or instead of, the cord (e.g., cord 100) described above. Further, the curable material could be formed of any other type of material which provides a desired property such as stiffness, resiliency, or flexibility to a supporting structure. In another example a supporting structure (e.g., structure 10) may receive a hydrophilic or expandable material for providing structure and/or resiliency to the supporting structure. A hydrophilic material could be encased in a permeable material and such material would swell and become stiffer as it absorbs water from pathway 15 when received therein. In a further example, a slurry of metallic particles could be received in supporting structure 10 to provide structure and/or resiliency thereto. The slurry of metallic particles may become stiffer by applying an electrical current thereto as described in co-owned U.S. patent application Ser. No. 11/170,554, entitled "Fixation Systems with Modulated Stiffness", and filed on Jun. 30, 2005.

A plurality of segments (e.g., segment 50 and segment 60) of a supporting structure (e.g., supporting structure 10) may be configured (e.g., shaped and dimensioned) such that the supporting structure (e.g., supporting structure 10) as a whole (i.e., when the segments are connected to, or engaged with, one another) has a shape which promotes a correct curvature of a spine of the patient into which structure 10 is inserted. For example, each of such individual segments may have differing individual shapes and sizes to allow the supporting structure as a whole to have a particular desired shape. The shape of the individual segments, and/or supporting structure as a whole, may promote the correct curvature of the spine of a patient having scoliosis or another undesirable curvature of the spine.

Also, the supporting of the spine described above by a supporting structure (e.g., supporting structure 10) could include distracting portions (e.g., vertebrae) of a spine relative to one another. For example, such distraction may be utilized in the event of a patient having a collapsed disc, e.g., an acute fractured collapsing disc. Also, the supporting structure could provide such distraction while being flexible at other locations with the spinal column for example, an end (e.g., end 110) of a supporting structure (e.g., supporting structure 10) may provide such distraction by supporting a disc or vertebra adjacent a damaged disc while the remainder of the supporting structure could remain flexible and/or resilient.

Figure 6:
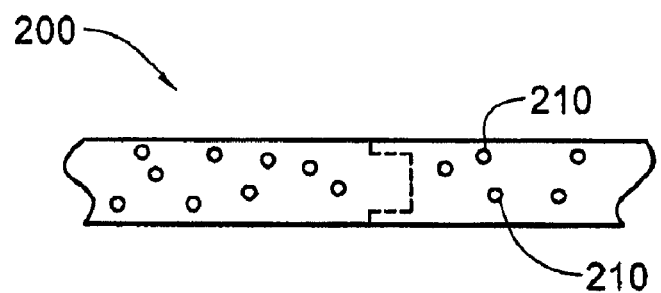
FIG. 6 is a side elevational view of another embodiment of a portion of a supporting structure further including a plurality of leaching holes, in accordance with an aspect of the present invention.

In another example, a supporting structure 200 could include a plurality of radial openings 210 as depicted for example in FIG. 6. The openings may allow the leaching of fusion-promoting proteins (e.g., BMP) from an interior (not shown) of the supporting structure to an exterior thereof in spinal column 20. The proteins may stimulate fusion of the supporting structure with one or more vertebrae of spinal column 20 thereby promoting the support and/or correct curvature of the vertebrae of the spinal column. Similar to supporting structure 10, supporting structure 200 may be formed of a plurality of segments (e.g., segment 250 and segment 260). When such fusion-promoting proteins are utilized such that they may leach from the interior of the supporting structure into the pathway or spinal column, the supporting structure would permanently remain (i.e., not be removed) within spinal column 20 to provide support thereto.

In a further example, a continuous and/or uniform (e.g., not formed of a plurality of segments) supporting structure (not shown) could be inserted into a pathway (e.g., pathway 15). Such continuous and/or uniform supporting structure could include a cutting tool or could be inserted into such a pathway created in another manner. Also, a flowable curable biocompatible material may be inserted or injected into a cavity (not shown) of the continuous and/or uniform supporting structure to provide the described support and/or resiliency thereto. Further, the continuous and/or uniform supporting structure could be flexible and/or resilient. Moreover, the cavity of such a continuous and/or uniform supporting structure could receive a hydrophilic material, expandable material, or a slurry of metallic particles as described above.

Figure 8:
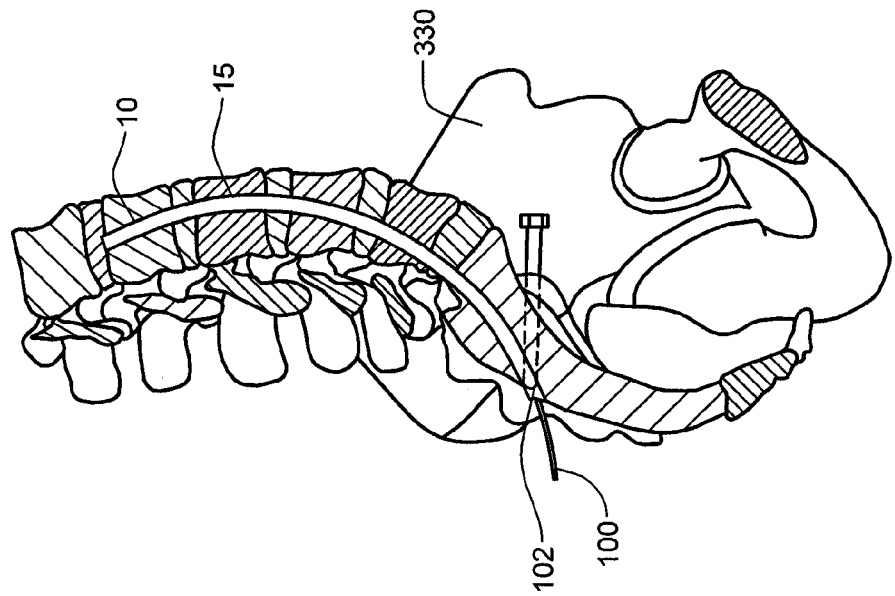
FIG. 8 is a side cross-sectional view of the supporting structure and connecting portions of FIG. 7.
Figure 7:
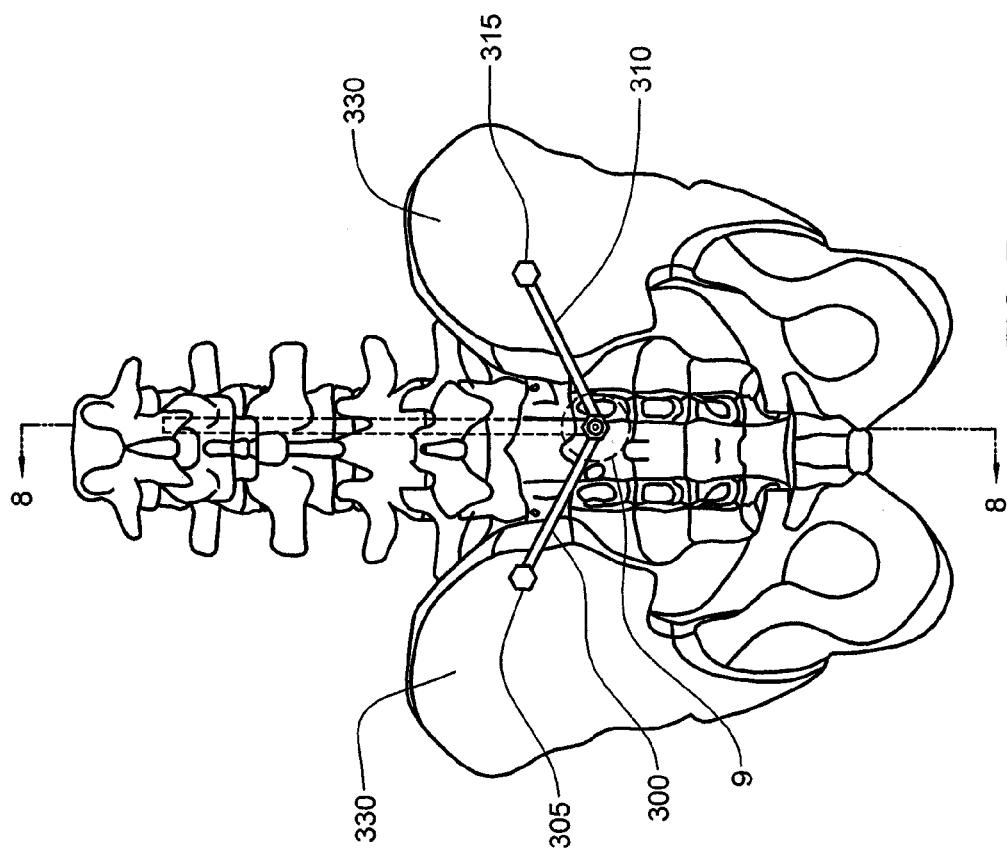
FIG. 7 is a rear elevational view of another embodiment of the supporting structure of FIG. 1 further including connecting portions connecting the supporting structure to the ilium.
Figure 9:
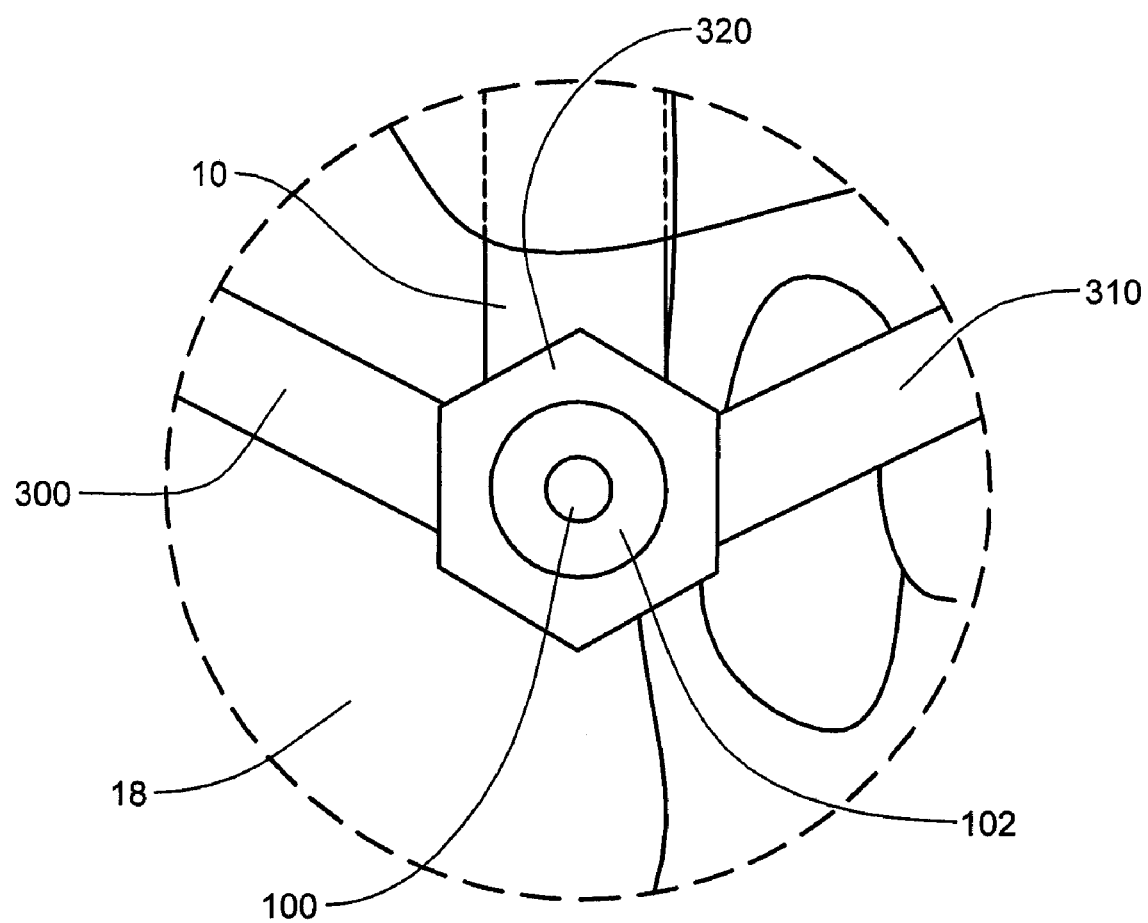
FIG. 9 is an enlarged elevational view of a portion of the structure and connecting portions of FIG. 7.

In yet another example as depicted in FIGS. 7-9, supporting structure 10 may have an end 102 which is configured (e.g., threaded) to engage a nut 320 or other means of fastening to structure 10. End 102 and nut 320 may be connected to lateral connectors 300 and 310 which may also be connected to anchors or screws 305 and 315 connected to opposite portions of an ilium 330. The connection of connectors 300 and 310 to end 102 inhibits movement (e.g., rotation and/or lateral movement) of supporting structure 10 within spinal column 20 by anchoring structure 10 to ilium 330. For example, the connection of structure 10 to ilium 330 via connectors 300, 310 and screws 305, 315 may inhibit movement of structure 10 within pathway 15 and laterally in a direction perpendicular to pathway 15. Further, in an unillustrated embodiment, cord 100 could engage with a nut, such as nut 320, to tighten segments (e.g., segment 50 and segment 60) of structure 10 relative to each other to promote rigidity and stiffness of structure 10. In such an example, cord 100 could be threaded (e.g., have external threads to engage nut 320) and could be made of a material which is flexible enough to allow it to be threaded (e.g., inserted) within structure 10 but also rigid enough to supply resistance to a tightening of nut 320. Also, structure 10 could be connected to ilium 330, or another bone in the vicinity of pathway 15 to provide stability to structure 10 in any number of other ways which inhibit movement of structure 10.

Also, it will be understood to one skilled in the art that a supporting structure (e.g., structure 10) may be inserted into and/or be located at any of various locations within spinal column 20 and may provide support thereto. For example, instead of being inserted through sacrum 18 as described above, the supporting structure may be inserted into spinal column 20 at another point along the spinal column to provide support and/or correction of the curvature of the spinal column. Also, in addition to the creation of the pathway (e.g., pathway 15) described above via a cutting tool, such pathway could be formed in any manner known by those skilled in the art which creates a pathway having a desired size and dimension for receiving a supporting structure (e.g., supporting structure 10) for supporting, and/or correcting the curvature of, the spinal column. Further, the supporting structure could be formed of any number of materials which is biocompatible and capable of providing such support and curvature correction. Moreover, the pathway could be created utilizing a lateral x-ray image of spinal column 20. Thus, some or all of the supporting structure may be formed of a material visible to such a lateral x-ray. Further, it will be understood by one skilled in the art that a supporting structure (e.g., supporting structure 10, supporting structure 200) could be formed in any shape (e.g., a cylindrical shape, a tubular shape, a continuous or non-continuous shape) which allows the supporting structure to support and/or correct a curvature of a spinal column.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A method for use in supporting a spine, the method comprising:
   forming a pathway in a spine by removing a plurality of portions of a plurality of vertebrae of the spine with a supporting structure including a cutting tool on a front end of the supporting structure, the supporting structure comprising a plurality of segments oriented in a non-interconnected state;
   stiffening the supporting structure by orienting the plurality of segments in an interconnected state in the pathway along the plurality of vertebrae to provide structure to the spine to promote a correct curvature of the spine; and inhibiting movement of the stiffened support structure in the pathway by connecting the supporting structure to an anchor secured to bony structure adjacent the pathway.

2. The method of claim 1, wherein the stiffening the supporting structure comprises engaging ends of the plurality of segments with each other.

3. The method of claim 2, wherein the stiffening the supporting structure further comprises tightening a cord inserted within a cavity of the plurality of segments.

4. The method of claim 1, further comprising the step of injecting a curable material into a cavity of the supporting structure and allowing the material to cure to stiffen the supporting structure.

5. The method of claim 1, wherein the stiffening the supporting structure further comprises distracting a first vertebra of the plurality of vertebrae from a second vertebra of the plurality of vertebrae.

6. The method of claim 1, wherein the removing the plurality of portions comprises removing a portion from a sacrum and a plurality of lumbar vertebrae of the spine.

7. The method of claim 1, wherein the forming the pathway comprises forming the pathway utilizing a lateral X-ray image of the spine to determine a desired direction of the pathway through the spine when removing the plurality of portions of the plurality of vertebrae of the spine.

8. The method of claim 1, wherein the forming the pathway comprises utilizing the cutting tool on the front end of the supporting structure to remove the plurality of portions of the plurality of vertebrae of the spine to form the pathway.

9. The method of claim 1, further comprising providing openings in the supporting structure to promote leaching of fusion stimulating proteins from an interior of the supporting structure.

10. The method of claim 1, wherein the forming the pathway comprises forming the pathway to have a shape promoting a correct curvature of the spine.

11. The method of claim 1, wherein the supporting structure comprises a tubular supporting structure.

12. The system of claim 1, wherein a first end of the segments includes a narrowed end and a second end of the segments include a receiving end, wherein when the segments are interconnected the narrowed end of one respective segment fits within the receiving end of another segment.

13. The method of claim 1, wherein the forming the pathway comprises utilizing the cutting tool on the front end of the supporting structure to remove the plurality of portions of the plurality of vertebrae of the spine to form the pathway, and further comprising removing the cutting tool through the interior of the support structure after forming the pathway.

14. The method of claim 1, wherein:

the stiffening the supporting structure further comprises tightening a cord inserted within a cavity of the plurality of segments; and inhibiting movement of the stiffened support structure includes threading the anchor to an end of the cord.

15. A spine-supporting structure system comprising:

a supporting structure for supporting a spine comprising a plurality of segments, each of said plurality of segments having a first end sized and configured to be received within a second end of another segment of said plurality of segments and wherein said plurality of segments are connected to each other to form an elongated shape promoting a correct curvature of the spine, wherein when said segments are connected to each other it causes said support structure to stiffen in said shape;

wherein the support structure is sized and configured to fit within a pathway formed through a plurality of vertebrae of the spine; and wherein said supporting structure includes a cutting tool on a front end of said supporting structure, said cutting tool configured to remove a portion of the plurality of vertebrae of the spine to form the pathway;

wherein said cutting tool is connected to a cord extending through said supporting structure to a rear end of said supporting structure so that said cutting tool is removed through an interior of said support structure after forming the pathway.

16. The system of claim 15, further comprising a first segment of said plurality of segments and a second segment of said plurality of segments, wherein said end of said first segment has a diameter smaller than said second end of said second segment.

17. The system of claim 15, wherein said supporting structure comprises a cavity and said cord is located in said cavity.

18. The system of claim 15, wherein said supporting structure comprises a cavity and a curable material injected into said cavity to stiffen the supporting structure.

19. The system of claim 15, wherein said supporting structure comprises a plurality of openings providing communication between an interior of said supporting structure and said pathway to promote leaching of fusion stimulating proteins from said interior to the pathway.

20. The system of claim 15, wherein said supporting structure comprises a tubular supporting structure.

21. The system of claim 15, wherein the pathway comprises a pathway through a sacrum and a plurality of lumbar vertebrae of the spine.

22. A supporting structure system for a spine, the system comprising:

a plurality of segments configured to form a supporting structure and configured to be inserted into a spinal pathway created in a plurality of vertebrae of the spine;

a first segment of said plurality of segments having a first end and a second end;

a second segment of said plurality of segments having a third end and a fourth end;

said first end engageable with said third end to connect said first segment to said second segment;

a cord received in a first interior of said first segment and a second interior of said second segment, said cord coupled to said first segment and said second segment and providing stiffness to said first segment and said second segment to support the spine when said plurality of segments is inserted into the spinal pathway; and a cutting tool located on an end of at least one of said first segment and said second segment to allow the pathway to be created by a user manipulating the system; and an anchor threadingly engaged to said cord that is engageable to bony structure of the spine to inhibit movement of said support structure when inserted into the spinal pathway.

23. The system of claim 22, wherein said cord provides stiffness to said first segment and said second segment and allows movement of said first segment relative to said second segment to provide flexibility to said supporting structure.

24. The system of claim 22, further comprising a curable material in said first interior and said second interior to provide at least one of stiffness and flexibility to said first segment and said second segment.

25. The system of claim 22, further comprising radial holes in at least one of said first segment and said second segment to allow fluid communication of fusion-promoting materials from at least one of said first interior and said second interior to the pathway.

* * * * *